United States Patent [19]
Reed et al.

[11] Patent Number: 5,915,283
[45] Date of Patent: Jun. 22, 1999

[54] METALLIC SHEET INSULATION SYSTEM

[75] Inventors: Kevin J. Reed, Landenberg, Pa.;
Robert L. Danley, Collingswood, N.J.;
John W. Schaefer, Wilmington, Del.

[73] Assignee: TA Instruments, Inc., New Castle, Del.

[21] Appl. No.: 08/769,540

[22] Filed: Dec. 19, 1996

Related U.S. Application Data

[63] Continuation-in-part of application No. 08/609,547, Mar. 1, 1996, Pat. No. 5,710,426.

[51] Int. Cl.$^6$ ..................................................... G01N 1/00
[52] U.S. Cl. ........................................................ 73/863.11
[58] Field of Search .............................. 73/863.11, 865.6, 73/865.8; 374/45–52; 220/445–447; 373/113

[56] References Cited

U.S. PATENT DOCUMENTS

| | | |
|---|---|---|
| 1,652,525 | 12/1927 | Hahnemann et al. ..................... 374/47 |
| 2,695,744 | 11/1954 | Gattuso . | |
| 3,082,900 | 3/1963 | Goodman . |
| 3,365,092 | 1/1968 | Blessing . |
| 3,981,689 | 9/1976 | Trelease . |
| 4,923,081 | 5/1990 | Weaver et al. . |
| 5,015,825 | 5/1991 | Brindley ..................................... 374/50 |
| 5,595,319 | 1/1997 | Householder et al. . |

*Primary Examiner*—Robert Raevis
*Attorney, Agent, or Firm*—Crowell & Moring LLP

[57] ABSTRACT

A heat shield and insulation system comprised of multiple layers of metallic sheets separated by small protrusions or dimples in the metallic sheets. The multiple layers are formed by spirally winding a coil of the metallic sheet around the sample enclosure. The protrusions are formed by stamping the metallic sheets, preferably in a random patterns, such that one set of protrusions does not nest in the protrusions formed in a neighboring sheet. The spacing between the layers of metallic sheets is small, such that convection does not occur in the space between the layers. Accordingly, the heat transfer between the layers of the metallic sheets is primarily radiative or via thermal conduction through the gas. The two ends of the helically wound metallic sheet are insulated by multiple thin metallic disks.

30 Claims, 2 Drawing Sheets

METALLIC SHEET INSULATION SYSTEM

The present application is a continuation-in-part of application Ser. No. 08/609,547, filed on Mar. 1, 1996, issued on Jan. 20, 1998 as U.S. Pat. No. 5,710,426.

BACKGROUND

1. Field of the Invention

The present invention relates to insulation systems used in thermal analysis instruments such as dynamical mechanical analyzers (DMAs) and other scientific or technical apparatus.

2. Background of the Invention

The present invention will be described primarily as it is used with dynamic mechanical analyzers (DMAs), as described in application Ser. No. 08/609,547, the parent of the present application, which is incorporated herein by reference. However, it may be incorporated in other apparatus for which the thermal sheet insulation system offers an advantage over conventional insulation systems, e.g., because the instruments will be used at sub-ambient temperatures, or because conventional insulation cannot tolerate the experimental conditions.

The sample and the fixtures in DMAs and TMAs are enclosed within a temperature-controlled sample chamber which can heat the sample and the fixtures to temperatures above normal ambient temperatures or cool the sample and the fixtures to temperatures below normal ambient temperatures. The temperature is generally varied dynamically, e.g., at a constant heating or cooling rate.

The sample chamber heats or cools the sample and fixtures, and provides a protective atmosphere to prevent sample degradation. Resistive heating elements can be located within the sample enclosure heating the sample and its fixtures directly, or they can be located external to the sample enclosure, heating air which is passed through the sample enclosure by a fan.

The sample and fixtures are cooled by introducing a cryogenic liquid or gas, generally nitrogen, into the sample chamber. When the cooling medium is a gas, the liquid cryogen is evaporated external to the sample chamber and the cold gas is transmitted to the sample chamber. When the cooling medium is a liquid, the liquid cryogen is transmitted to the sample chamber where it evaporates and cools the sample and its fixtures. Because the evaporation of a cryogenic liquid absorbs a large quantity of energy, a much greater cooling effect is available when using evaporation of the cryogen within the sample chamber, leading to a much lower consumption of the cryogen. Unfortunately, the difference in temperature between the liquid and the gas is large, so that the evaporation process can cause large temperature variations within the sample chamber, which in turn can cause large and erratic variations of the sample temperature.

Because DMAs are often operated at temperatures well below room temperature, condensation of atmospheric moisture within the sample chamber can occur. In most cases, the sample region is purged with a dry gas to prevent this moisture from contaminating the sample. Conventional DMAs use prior art fibrous thermal insulation to maintain the low or high temperature of the sample region. Although fibrous insulation is a very effective thermal insulator, it also absorbs moisture from atmospheric condensation very readily. When the sample chamber is cooled, this moisture freezes, forming ice which reduces the effectiveness of the insulation. Later on, when the DMA is heated up, the ice melts and may drip into the sample region and may contaminate the sample.

SUMMARY OF THE INVENTION

The present invention is a heat shield and thermal insulator formed by a coil of a thin metallic sheet, e.g. stainless steel. As shown in FIG. 1, the metallic sheet is wound around a cooling jacket in a spiral fashion. Stainless steel is the preferred material for the metallic sheet insulator of the present invention, although material other than stainless steel could be used. The material must have a low thermal emissivity, and must be otherwise appropriate for the intended temperature range. For example, if the instrument is not intended to be used at relatively high temperatures, the sheet could be an aluminum sheet. If the instrument were intended only for low-temperature operation, a sheet of metallized mylar could be used. The metallic sheet forms multiple layers which are separated by small protrusions formed in the metallic sheet by stamping. In one embodiment of the present invention, the protrusions are applied along a vertical straight line, but the distance between consecutive straight lines of protrusions is preferably variable, such that nesting of one set of protrusions into the dimples formed by the protrusions on a neighboring sheet cannot occur, except in isolated instances.

The metallic sheet insulates the cooling jacket by greatly reducing heat exchange by radiation and by eliminating convection in the gas spaces between layers. It limits heat transfer to radiation and conduction through the gas layers. Because gases are very poor thermal conductors, and because the many layers greatly reduce radiative heat exchange, the transfer of heat from the ambient to the cooling jacket is low. The spacing of the layers must be kept small enough such that convection cannot develop in the spaces between layers. If the spacing is too large, heat convection will occur and the rate of heat transfer through the gas will increase dramatically—as much as ten times or more. If the spacing is too small, too much metallic sheet would have to be used.

The spacing between layers can be increased if the number of layers is increased, which would provide improved insulation. However, this would also result in a system having higher mass, and is therefore less responsive thermally. Thus the speed at which temperature changes could be made would be reduced.

The ends of the sample enclosure are also insulated by multiple layers of metallic sheets. Disks of thin metallic sheets are stacked to form a multilayer metallic insulation system. At the top end, smaller diameter disks fit inside of the insulation formed by the wound sheet, while larger diameter disks cover the edges of the wound sheet. The overlapping intersection prevents excessive heat loss through the edges of the hottest layers of the metallic sheet insulation system. At the bottom of the enclosure, small diameter disks fit inside of the wound metallic sheet, while larger diameter disks cover the edges of metallic sheet. Also, by overlapping the wound sheet with the large diameter disks at the top and the bottom, convective heat transfer between the layers of the wound sheet due to "chimney" effects is eliminated. The thickness of the disks is dictated by their mechanical properties. The disks must be sufficiently stiff such that they do not vibrate while the instrument is running. However, thicker disks have greater mass, which reduces the instrument's thermal responsiveness.

The entire assembly is enclosed by an outer jacket. The cooling gas which is introduced to the sample region, exits through an opening through the stack of upper metallic disks and then through an exhaust stack. Cooling gas which exits the cooling jacket at the top flows between the smaller diameter upper metallic disks inward to the exhaust stack and then out of the enclosure (as described below with reference to the Figures). To prevent recirculation of the exhausted cooling gas and infiltration of air from the surroundings, one of the large diameter upper disks is sealed to the outer jacket.

The metallic sheet insulation system described above is very nearly as efficient as conventional fibrous insulation systems. Unlike fibrous insulation systems, which have a huge surface area compared with the metallic sheet insulation system and are porous, the metallic sheet insulation system does not absorb significant quantities of moisture. Furthermore, once moisture is absorbed in a fibrous insulation system, it takes a long time to leave the system. The remaining moisture could contaminate the sample, or could result in water dripping into the sample chamber or elsewhere, or ice formation within the insulation, or elsewhere.

DETAILED DESCRIPTION OF THE INVENTION

The present invention is described in detail herein in terms of a single specific preferred embodiment of the invention, as it is used in a DMA. However, one skilled in the art could readily incorporate the present invention in other thermal analysis, technical or scientific apparatus.

Figure 1:
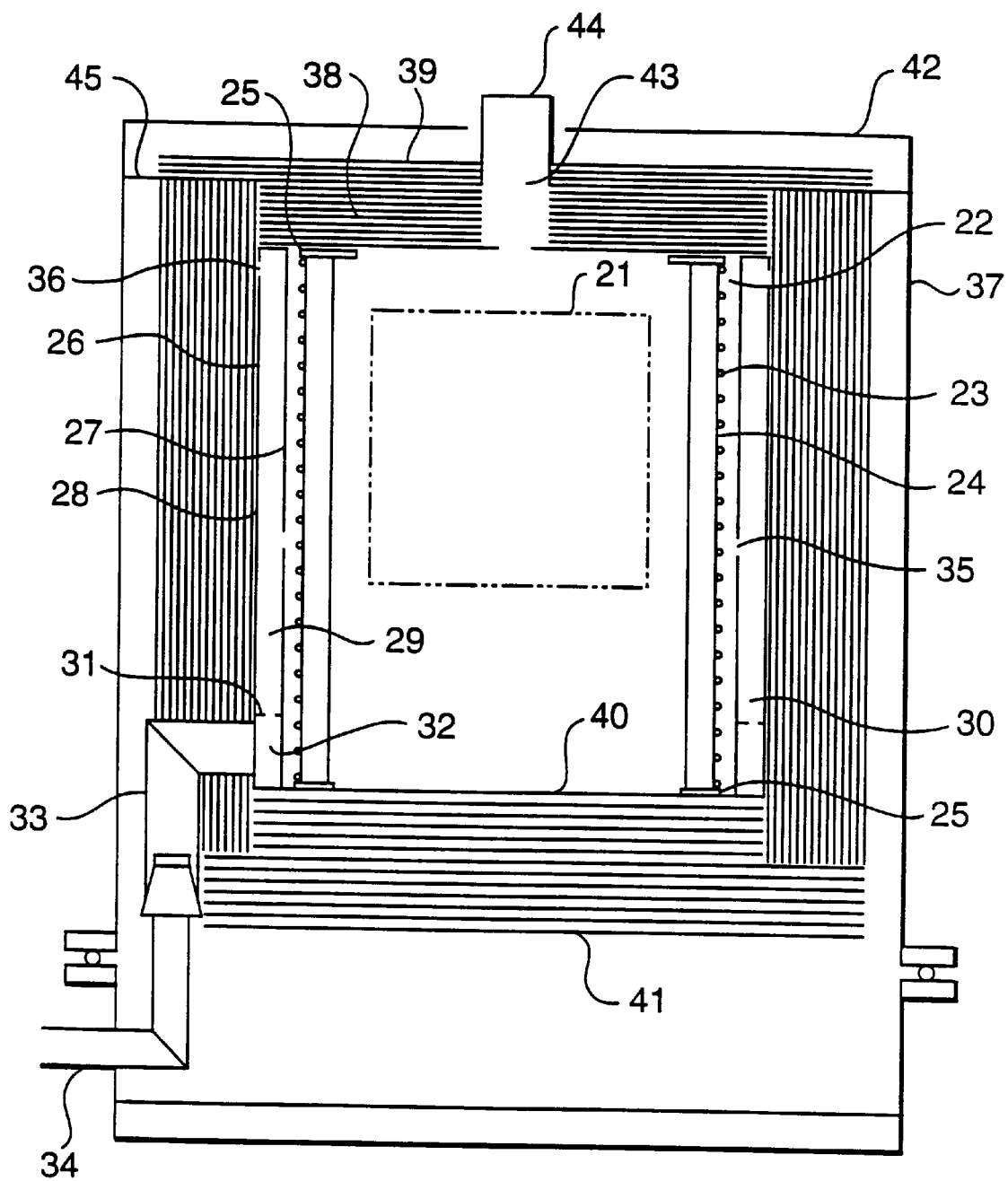
FIG. 1 is a schematic vertical cross sectional diagram showing the present invention as it is used in a thermal analysis instrument.

FIG. 1 is a vertical cross section through the centerline of the sample chamber of a DMA. Sample zone 21 is surrounded by a heating assembly 22 comprised of a resistive heating element 23 which is wound in a spiral around eight ceramic insulator rods 24. The insulator rods are connected at each of their ends to rings 25, thus forming a cage-like heater assembly. An electric current flowing through heating element 23 generates heat by Joule heating. The heat is transmitted to the sample zone by radiation, conduction and convection.

Heating assembly 22 is surrounded by cooling jacket 26. Cooling jacket 26 is comprised of inner cylinder 27 and outer cylinder 28—the inner and outer cylinders being connected at their extremities to form an annular cavity. The annular cavity is divided into an upper chamber 29 and a lower chamber 30 by divider 31. Divider 31 is perforated by a series of holes 32 uniformly distributed about its middle circumference. Cooling gas is supplied to the lower chamber 30 through the gas supply tube 33, which is supplied by the connector 34. Gas passes from the lower chamber to the upper chamber through the holes in the divider. The cooling gas flows upward in the upper chamber 29 of cooling jacket 26, cooling the sample zone. A small fraction of the cooling gas is discharged into the sample chamber through a series of small holes 35 (ranging from 0.035 inch diameter holes to 0.060 inch diameter holes, preferably 0.043 inch diameter holes) through the inner wall of the cooling jacket. This small fraction of the cooling gas ensures that the sample environment is adequately cooled, but is small enough that it will not impose drag forces on thin samples. The remainder of the cooling gas continues upward through the upper chamber of the cooling jacket and exits the cooling jacket through a series of large holes 36 equally spaced around the top of outer cylinder 28.

Cooling jacket 26 is insulated by a spirally-wound metallic sheet 37, e.g., a coil of thin stainless steel sheet. If stainless steel is used, the thickness of the sheet is preferably 0.002 inches thick, but it can range from 0.001 inches to 0.005. As discussed above, in some applications, material other than stainless steel could be used. Sheet 37, e.g., a 5" high, ten foot long sheet, forms, e.g., fifteen layers which are separated by small protrusions (ranging from 0.02" to 0.125", preferably 0.035", in height), at a density of approximately 0.5 per square inch to 2 per square inch, preferably one per square inch, formed in the stainless steel sheet by stamping. In one embodiment of the present invention, the protrusions are applied along a vertical straight line, but the distance between consecutive straight lines of protrusions is preferably variable, such that nesting of one set of protrusions into the dimples formed by the protrusions on a neighboring sheet cannot occur, except in isolated instances.

Metallic sheet 37 insulates cooling jacket 26 by greatly reducing heat exchange by radiation and by eliminating convection in the gas spaces between layers. It limits heat transfer to radiation and conduction through the gas. Because gases are very poor thermal conductors, and because the many layers greatly reduce radiant heat exchange, the transfer of heat from the ambient to the cooling jacket is low. The spacing of the layers must be kept small enough such that convection cannot develop in the spaces between layers. If the spacing is too large, heat convection will occur and the rate of heat transfer through the gas will increase dramatically—as much as ten times or more. If the spacing is too small, too much stainless steel sheet would have to be used.

The spacing between layers can be increased if the number of layers is increased, which would provide improved insulation. However, this would also result in a system having higher mass, and is therefore less responsive thermally. Thus the speed at which temperature changes could be made would be reduced.

The ends of the sample enclosure are similarly insulated. Thin metallic disks (e.g., stainless steel disks 0.005 to 0.015 inches thick) are stacked to form a multilayer metallic insulation system. At the top end, smaller diameter disks 38 fit inside of the insulation formed by the spirally-wound sheet, while larger diameter disks 39 cover the edges of the wound sheet. The overlapping intersection prevents excessive heat loss through the edges of the hottest layers of the metallic sheet system. At the bottom of the enclosure, small diameter disks 40 fit inside of the wound metallic sheet, while larger diameter disks 41 cover the edges of metallic sheet 37. Because the large diameter disks overlap the wound sheet, "chimney" effect convection is eliminated.

The entire assembly is enclosed by an outer jacket 42. The cooling gas which is introduced to the sample region exits through an opening 43 through the stack of upper metallic disks and then through exhaust stack 44. Cooling gas which exits the cooling jacket at the top flows between the smaller diameter upper metallic disks inward to the exhaust stack and then out of the enclosure. To prevent recirculation of the exhausted cooling gas and infiltration of air from the surroundings, one of the large diameter upper metallic disks 45 (which has a larger diameter than the other upper metallic disks) is sealed to the outer jacket.

Figure 2:
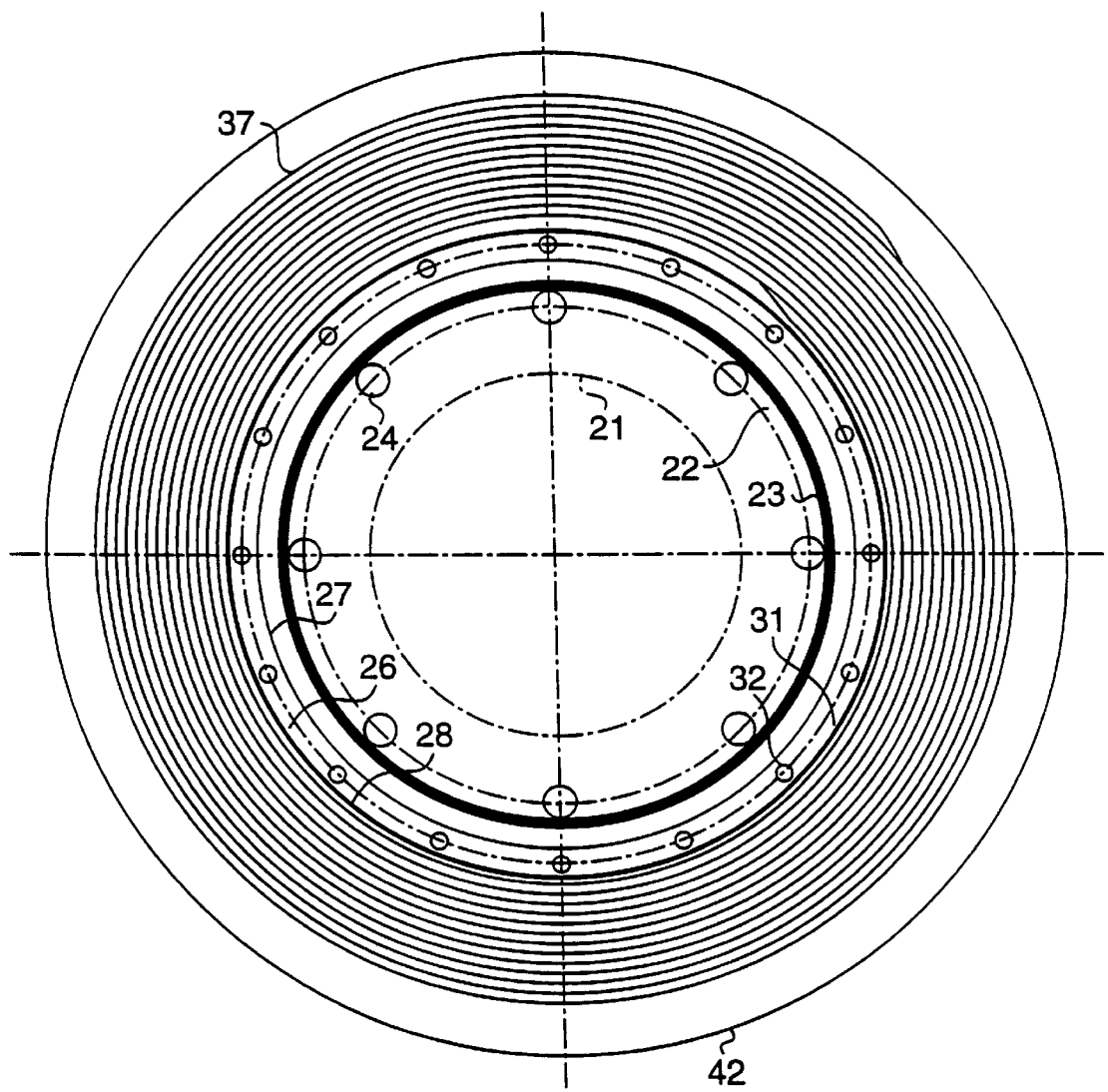
FIG. 2 is a schematic horizontal cross sectional diagram showing the present invention as it is used in a thermal analysis instrument.

FIG. 2 is a horizontal cross section through the sample chamber. Sample zone 21 is surrounded by heating assembly 22, which includes resistive heating element 23, wound in a spiral around eight ceramic insulator rods 24. The heater assembly is surrounded by the cooling jacket 26, which has inner wall 27 and outer wall 28. Gas flowing from the lower chamber to the upper chamber passes through the series of small holes 32. The total area of the holes through the divider is much smaller than the total cross sectional area of the lower chamber, preferably, less than 10% of the total area. This creates a pressure drop through the holes such that the pressure in the upper chamber is much lower than the pressure in the lower chamber. This ensures that gas flows into the upper chamber with a uniform distribution about the cooling jacket centerline. Coiled thin metallic sheet 37 surrounds the cooling jacket. The metallic sheet and the metallic disks are enclosed within outer jacket 42.

Although spirally-wound metallic sheet 37 is described herein as using protrusions formed by stamping the metallic sheet to provide the spacing between successive layers of the metallic sheet, there are other methods which may be used to achieve the same effect of providing the requisite space between the successive layers, i.e., a space which is too small for convection to occur between adjacent layers, but which has a very low direct heat conduction path. Methods for separating the layers of wound sheet fall principally into two groups: those which include forming of the sheet itself and those which include separate elements for spacing the layers, which may or may not be permanently attached to the wound sheet. The method of the present invention uses formed protrusions which are of spherical form. Alternately the sheet could be folded transversely to its length so that a series of ridges parallel to the centerline of the furnace are formed. The ridges are spaced so that ridges on adjacent layers do not nestle in one another, so that the desired separation of layers is achieved. Many other methods of forming the sheet may be used which achieve separation of the sheet in accordance with the current invention.

The use of distinct elements to separate the sheet may be exemplified by the use of small pieces of metal, e.g., blocks or disks, which are attached to the sheet by resistance welding. The blocks are spaced similarly to the protrusions. Other methods include small rods, bars or tubes inserted between layers of the wound sheet, disposed parallel to the furnace centerline. Separation of the sheet can be achieved by the methods described above, or by a variety of other methods which have the essential characteristic of maintaining the desired spacing between the layers so that convective heat transfer between the layers is prevented, and so that heat conduction through the interlayer gas is negligible.

The foregoing disclosure of an embodiment of the present invention has been presented for purposes of illustration and description. It is not intended to be exhaustive or to limit the invention to the precise forms or applications disclosed. Many variations and modifications of the embodiment and application described herein will be obvious to one of ordinary skill in the art in light of the above disclosure. The scope of the invention is to be defined only by the claims appended hereto, and by their equivalents.

What is claimed is:

1. An insulation system for a thermal analysis instrument comprising a sheet of a thin material that has low thermal radiation emissivity spirally wound around a sample chamber, said sheet comprising a plurality of small protrusions maintaining the separation between successive layers of the spirally wound sheet.

2. The insulation system of claim 1, wherein the small protrusions are in a series of straight lines of protrusions, and the distance between consecutive straight lines of protrusions is variable.

3. The insulation system of claim 1, further comprising a plurality of disks having a low thermal radiation emissivity forming a multilayer insulation system at a first end of the sample chamber, and a plurality of low thermal radiation emissivity disks forming a multilayer insulation system at a second end of the sample chamber.

4. The insulation system of claim 1, wherein the sheet of thin material having a low thermal radiation emissivity is a stainless steel sheet.

5. The insulation system of claim 4, wherein the thickness of the stainless steel sheet is between approximately 0.001 and 0.005 inches thick.

6. The insulation system of claim 4, wherein the height of the protrusions is between 0.020 and 0.125 inches.

7. The insulation system of claim 4, wherein the density of the protrusions is between approximately 0.5 protrusions per square inch to 2 protrusions per square inch.

8. The insulation system of claim 1, wherein the protrusions are variably positioned on the sheet.

9. The insulation system of claim 1, wherein the sheet is an aluminum sheet.

10. The insulation system of claim 1, wherein the sheet is a metallized mylar sheet.

11. A sample chamber comprising:
    (a) a sheet of thin metallic material having a low thermal radiation emissivity spirally wound around a cooling jacket;
    (b) a plurality of disks having a low thermal radiation emissivity forming a multilayer insulation system at a first end of the spirally wound metallic sheet, and a plurality of disks having a low thermal radiation emissivity forming a multilayer insulation system at a second end of the spirally wound metallic sheet.

12. The sample chamber of claim 11, wherein said sheet comprises a plurality of small protrusions maintaining the separation between successive layers of the spirally wound sheet.

13. The insulation system of claim 12, wherein the protrusions are variably positioned on the metallic sheet.

14. The sample chamber of claim 11, further comprising means for providing cooling fluid to the cooling jacket.

15. The sample chamber of claim 14, wherein the cooling jacket comprises an inner cylinder and an outer cylinder, said inner and outer cylinder forming an annular cavity, and wherein the means for providing cooling fluid to the cooling jacket provides cooling fluid to the annular cavity.

16. The sample chamber of claim 15, wherein the inner cylinder comprises a series of small holes, which allow a portion of the cooling fluid to pass into the center of the sample chamber.

17. The sample chamber of claim 11, wherein the spacing between successive layers of metallic sheets is selected such that convection cannot occur between the successive layers.

18. The sample chamber of claim 11, wherein the metallic sheet is an aluminum sheet.

19. The sample chamber of claim 11, wherein the metallic sheet is a metallized mylar sheet.

20. The sample chamber of claim 11, further comprising a cylindrical outer jacket enclosing the spirally wound metallic sheet.

21. A thermal analysis instrument comprising:
    (a) a sample zone;
    (b) a cooling jacket surrounding the sample zone, said cooling jacket comprising an inner cylinder and an outer cylinder, said inner and outer cylinders forming an annular cavity;

(c) a metallic sheet spirally wound around said cooling jacket, forming a plurality of metallic layers surrounding the cooling jacket; and (d) a first plurality of flat metallic disks at a first end of the spirally wound metallic sheet, and a second plurality of metallic disks at a second end of the spirally wound metallic sheet, wherein the spirally wound metallic sheet and the first and second plurality of flat metallic disks enclose the cooling jacket.

22. The thermal analysis instrument of claim 21, wherein the first plurality of flat metallic disks comprises a third plurality of metallic disks having a diameter equal to the inside diameter of the spirally wound metallic sheet, and a fourth plurality of metallic disks having a diameter equal to the outside diameter of the spirally wound metallic sheet, and wherein the second plurality of flat metallic disks comprises a fifth plurality of metallic disks having a diameter equal to the inside diameter of the spirally wound metallic sheet, and a sixth plurality of metallic disks having a diameter equal to the outside diameter of the spirally wound metallic sheet.

23. The thermal analysis instrument of claim 21, wherein the thermal analysis instrument is a dynamic mechanical analyzer or a thermal mechanical analyzer.

24. The thermal analysis instrument of claim 21, further comprising means for introducing a cooling fluid to the annular cavity.

25. The thermal analysis instrument of claim 24, wherein the inner cylinder of the cooling jacket comprises a series of small holes, which allow cooling fluid to pass from the annular cavity into the sample zone.

26. The thermal analysis instrument of claim 21, wherein the spacing between successive layers of metallic sheets is selected such that convection does not occur between the successive layers of metallic sheets.

27. The thermal analysis instrument of claim 21, wherein the spirally wound metallic sheet is a sheet of stainless steel.

28. The thermal analysis instrument of claim 21, wherein the spirally wound metallic sheet comprises a plurality of small protrusions which maintain the separation between successive layers of the metallic sheet.

29. The thermal analysis instrument of claim 21, further comprising a plurality of protrusions variably positioned on the metallic sheet.

30. The thermal analysis instrument of claim 21, further comprising a heating element surrounding the sample zone.

* * * * *